(12) United States Patent
Burger

(10) Patent No.: US 12,306,373 B2
(45) Date of Patent: May 20, 2025

(54) LOW MELTING POINT IONIC LIQUIDS FOR INFRA-RED LIQUID LENS DESIGN

(71) Applicants: CORNING INCORPORATED, Corning, NY (US); LG INNOTEK CO., LTD., Gangseo-Gu (KR)

(72) Inventor: Benjamin Jean-Baptiste Francois Burger, Lyons (FR)

(73) Assignee: CORNING INCORPORATED, Corning, NY (US)

( * ) Notice: Subject to any disclaimer, the term of this patent is extended or adjusted under 35 U.S.C. 154(b) by 890 days.

(21) Appl. No.: 17/426,914

(22) PCT Filed: Jan. 23, 2020

(86) PCT No.: PCT/US2020/014694
§ 371 (c)(1),
(2) Date: Jul. 29, 2021

(87) PCT Pub. No.: WO2020/159781
PCT Pub. Date: Aug. 6, 2020

(65) Prior Publication Data
US 2022/0099862 A1    Mar. 31, 2022

Related U.S. Application Data

(60) Provisional application No. 62/800,088, filed on Feb. 1, 2019.

(51) Int. Cl.
| | |
|---|---|
| G02B 1/06 | (2006.01) |
| C01C 3/16 | (2006.01) |
| C07C 255/05 | (2006.01) |
| C07D 233/58 | (2006.01) |
| C07D 295/037 | (2006.01) |
| G02B 3/14 | (2006.01) |
| G02B 26/00 | (2006.01) |

(52) U.S. Cl.
CPC ............... G02B 1/06 (2013.01); C01C 3/16 (2013.01); C07C 255/05 (2013.01); C07D 233/58 (2013.01); C07D 295/037 (2013.01); G02B 3/14 (2013.01); G02B 26/005 (2013.01); G02B 2207/115 (2013.01)

(58) Field of Classification Search
CPC .......... G02B 1/06; G02B 3/14; G02B 26/005; C07D 295/037; C07D 233/58; C01C 3/16; C07C 255/05
See application file for complete search history.

(56) References Cited

U.S. PATENT DOCUMENTS

| | | |
|---|---|---|
| 2009/0052004 A1 | 2/2009 | Nakano et al. |
| 2017/0363930 A1 | 12/2017 | Ryu et al. |
| 2019/0023814 A1 | 1/2019 | Flack et al. |

FOREIGN PATENT DOCUMENTS

| | | | |
|---|---|---|---|
| CN | 102103220 A | | 6/2011 |
| CN | 102466825 A | * | 5/2012 |
| CN | 109280186 A | | 1/2019 |

OTHER PUBLICATIONS

Hu et al., Soft Matter, (2011), v.7, p. 5941-5943.*
Hu et al., Soft Matter, (2011), v.7, p. 5941-5943, Supporting information.*
Sigma Aldrich Catalog of product "Trihexyltetradecylphosphonium bis(trifluoromethylsulfonyl)amide" downloaded Nov. 10, 2024.*
Wippermann et al., downloaded through Research Gate, published in 2007.*
International Search Report and Written Opinion of the International Searching Authority; PCT/US2020/014694 Mailed on Aug. 18, 2021, 16 pages; European Patent Office.
Nanayakkara et al., "The Effect of AC Frequency on the Electrowetting Behavior of Ionic Liquids", Analytical Chemistry, vol. 82, No. 8, Apr. 15, 2010, pp. 3146-3154.
Xiaodong Hu et al., "Ionic liquid based variable focus lenses", Soft Matter, vol. 7, No. 13, Jan. 1, 2011, pp. 5941-5943.
Yoshida et al., "Ionic Liquids Based on Dicyanamide Anion:? Influence of Structural Variations in Cationic Structures on Ionic Conductivity" journal of physical chemistry part B, vol. 111, No. 18, May 2007, pp. 4742-4749.
Chinese Patent Application No. 202080027288.5, Office Action dated Feb. 24, 2024, 5 pages (English Translation only), Chinese Patent Office.

(Continued)

*Primary Examiner* — Yong L Chu

(57) ABSTRACT

A liquid lens can include a lens body forming a cavity with a conducting liquid and an insulating liquid disposed therein, the conducting liquid substantially immiscible with the insulating liquid to define an interface between the conducting and insulating liquids. The conducting liquid can include an ionic compound of either a dicyanamide anion and a cation counterion, or a tricyanomethanide anion and a cation counterion, the dicyanamide anion having the formula the tricyanomethanide anion having the formula and the cation counterion is one of an imidazolium, a pyrrolidininium, a piperidinium, a phosphonium, a pyridinium, a pyrrolinium or a sulfonium cation. The ionic compound of the conducting liquid can be N-methyl-N-ethylpyrrolidinium dicyanamide, 1-ethyl-3-methylimidazolium dicyanamide, 1-butyl-1-methylpyrrolidinium tricyanomethanide, or 1-ethyl-3-methylimidazolium tricyanomethanide, among others. The conducting liquid can have transmittance of at least 50% over a thickness of 1 mm for electromagnetic waves having wavelength of 1550 nm.

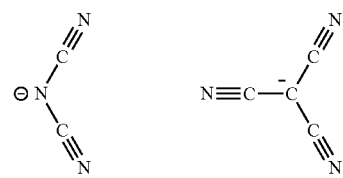

19 Claims, 7 Drawing Sheets

(56) References Cited

OTHER PUBLICATIONS

Taiwanese Patent Application No. 109102170, Office Action dated Dec. 27, 2023, 2 pages (English Translation only), Taiwanese Patent Office.
Xiaodong Hu, et al., "Electrowetting based infrared lens using ionic liquids", Appl. Phys. Lett. 99, 213505 (2011).

* cited by examiner

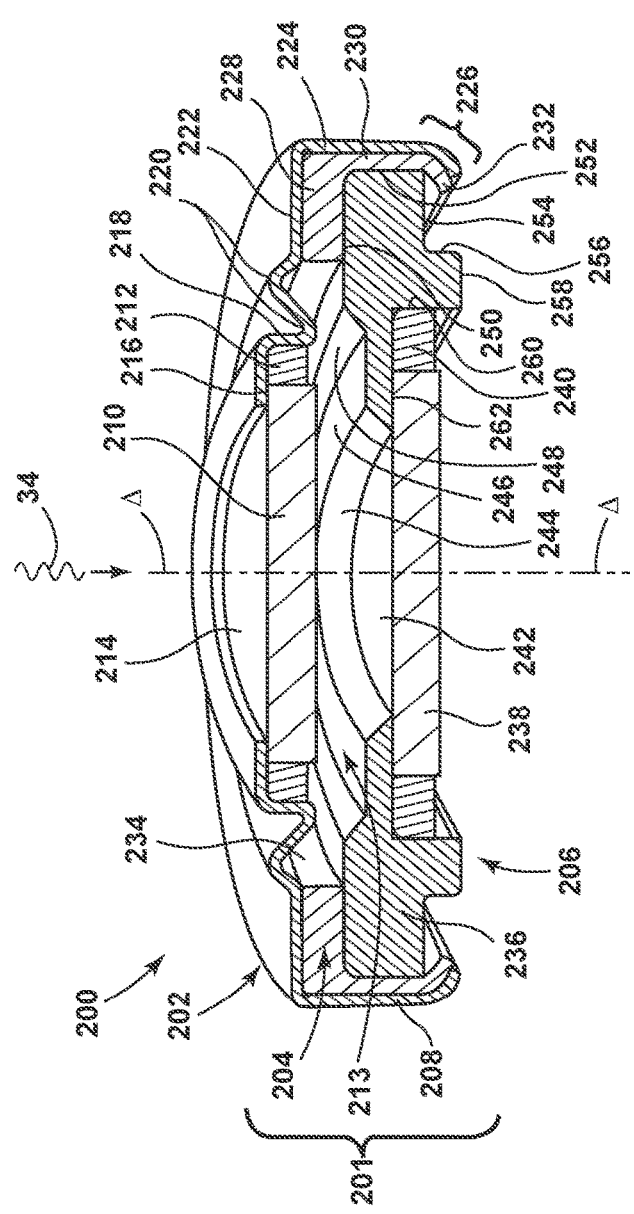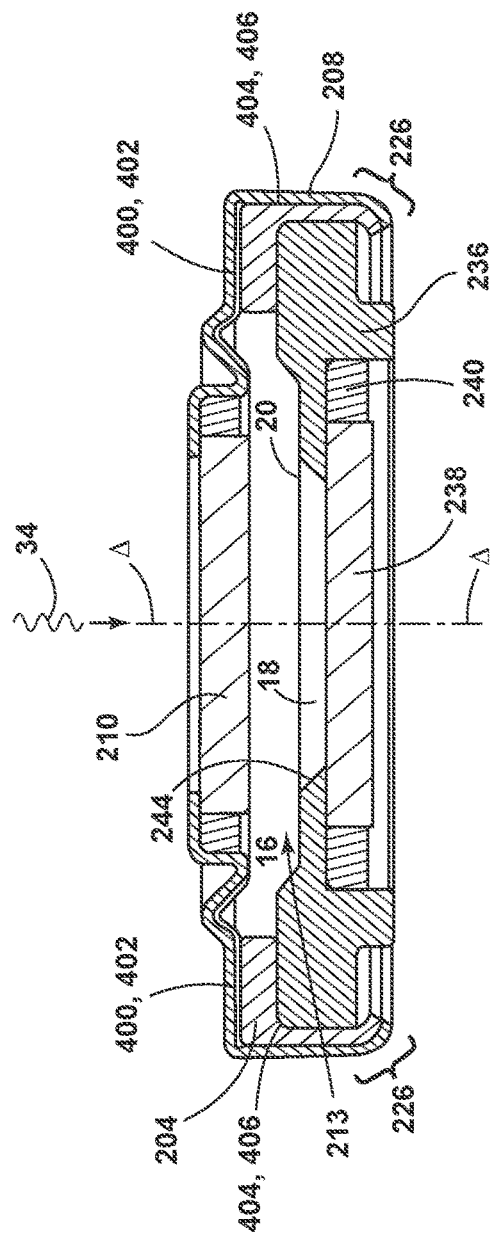
FIG. 2A
FIG. 2B

LOW MELTING POINT IONIC LIQUIDS FOR INFRA-RED LIQUID LENS DESIGN

CROSS-REFERENCE TO RELATED APPLICATIONS

This application is a national stage application under 35 U.S.C. § 371 of International Application No. PCT/US2020/014694, filed on Jan. 23, 2020, which claims the benefit of priority under 35 U.S.C. § 119 of U.S. Provisional Application Ser. No. 62/800,088 filed on Feb. 1, 2019 the content of which is relied upon and incorporated herein by reference in its entirety.

BACKGROUND

1. Field

This disclosure generally pertains to liquid lenses. More particularly, this disclosure pertains to the composition of a conducting liquid used with a liquid lens that transmits a high percentage of incident electromagnetic waves having a wavelength in the infrared portion of the electromagnetic spectrum.

3. Technical Background

Liquid lenses are a type of variable focus lenses that generally include a cavity with a conducting liquid and an insulating liquid disposed therein. The liquids are immiscible with each other and have different refractive indices such that the interface (e.g., the meniscus) between the liquids forms a lens. The cavity incorporates electrodes. The electrodes, based on the principles of electro-wetting, can manipulate the shape of the lens. For example, a voltage can be applied between the conducting liquid and a surface of the cavity to increase or decrease the wettability of the surface with respect to the conducting liquid and change the shape of the interface. Changing the shape (e.g., curvature) of the interface changes the focal length or focus of the lens.

Heretofore, the conducting liquid has typically included an ionic compound dissolved in water or another polar non-ionic solvent, with the ionic compound separating into the respective cation and anion, thus forming an electrically conductive liquid. The insulating liquid is typically an oil, an alkane, or a mixture of alkanes. The hydroxyl group (—OH) or groups present in the liquids typically used as the conducting liquid advantageously can make the conducting liquid immiscible with the typical liquids used for the insulating liquid.

For the liquid lens to operate optimally for the desired application, both the conducting liquid and the insulating liquid should be transparent to the wavelength of the incident electromagnetic waves desired to be sensed. In other words, the conducting liquid and the insulating liquid should not absorb the wavelength of the incident electromagnetic waves at issue. Absorbing the wavelength of the incident electromagnetic waves at issue prevents the transmission of the wavelength of the incident electromagnetic waves at issue through the liquid lens. Most of the applications that utilize a liquid lens are to sense (and image) the visible light portion of the electromagnetic spectrum having a wavelength between 400 nm and 700 nm. The conducting liquid typically used for those applications are highly transparent to incident electromagnetic waves having a wavelength within that range.

However, the conducting liquid typically utilized in liquid lenses can render the liquid lenses unsuitable for applications intended to sense incident electromagnetic waves having a wavelength longer than the wavelength of electromagnetic waves in the visible portion of the electromagnetic spectrum, such as electromagnetic waves in the infrared portion thereof.

Therefore, there is a need for a conducting liquid that is sufficiently transparent to electromagnetic waves having a wavelength longer than the visible region and also compatible with commonly used insulating liquids.

SUMMARY

The present disclosure satisfies that need by discovering that the dicyanamide anion and the tricyanomethanide anion can form ionic compounds with counterion cations that: (1) have a melting point of −20° C. or colder; (2) have a density closer to 1.0 g/cm$^3$ at 20° C. and thus are easier to pair with typically used insulating liquids; (3) are immiscible with typically used insulating liquids despite the lack of hydroxyl groups; and (4) are sufficiently transparent to electromagnetic waves having a wavelength longer than the visible region. Thus, such ionic compounds of the dicyanamide anion or the tricyanomethanide anion and a cation counterion make suitable conducting liquids for use with liquid lenses that are intended for applications to sense electromagnetic waves having a wavelength in the infrared region.

According to a first aspect of the present disclosure, a conducting liquid for a liquid lens comprises: an ionic compound of a dicyanamide anion and a cation counterion, the dicyanamide anion having the general formula

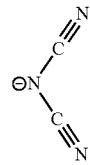

and the cation counterion is one of an imidazolium, a pyrrolidininium, a piperidinium, a phosphonium, a pyridinium, a pyrrolinium, a sulfonium cation, or any other cation ion providing the desired properties. In an embodiment, the conducting liquid is in the liquid phase between −20 degrees Celsius and 70 degrees Celsius. In an embodiment, the conducting liquid has a transmittance of at least 50% (including, in some embodiments, at least 85%) over a thickness of 1 mm for electromagnetic waves having a wavelength between 1400 nm and 1550 nm. In an embodiment, the cation counterion is an imidazolium cation having the general formula

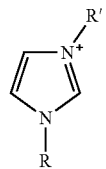

wherein, R is hydrogen or an alkyl group, and R' is hydrogen or any organyl group. In an embodiment, the imidazolium cation is one of 1-ethyl-3-methylimidazolium cation, 1-allyl-3-methylimidazolium, 1-benzyl-3-methylimidazolium, 1-butyl-3-methylimidazolium, 1-hexyl-3-methylimidazolium. In an embodiment, the imidazolium cation is 1-ethyl-3-methylimidazolium cation. In an embodiment, the cation counterion is a pyrrolidininium cation having the general formula

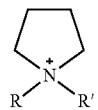

wherein R is hydrogen or an alkyl group, and R' is hydrogen or any organyl group. In an embodiment, the pyrrolidininium cation is one of N-ethyl-N-methylpyrrolidinium cation, 1-butyl-1-methylpyrrolidinium cation. In an embodiment, the pyrrolidininium cation is N-ethyl-N-methylpyrrolidinium cation. In an embodiment, the conducting liquid consists of one of the aforementioned ionic compounds, or a mixture of more than one of the aforementioned ionic compounds. In an embodiment, the conducting liquid comprises a mixture of one or more of the aforementioned ionic compounds and another liquid. In an embodiment, the conducting liquid comprises a mixture of one or more of the aforementioned ionic compounds and another liquid, wherein the one or more of the aforementioned ionic compounds is at least 50% by weight of the conducting liquid, at least 60% by weight of the conducting liquid, at least 70% by weight of the conducting liquid, at least 80% by weight of the conducting liquid, at least 90% by weight of the conducting liquid, or at least 99% by weight of the conducting liquid.

According to a second aspect of the present disclosure, a conducting liquid for a liquid lens comprises: an ionic compound of a tricyanomethanide anion and a cation counterion, the tricyanomethanide anion having the general formula

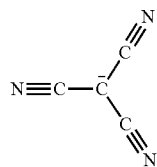

and the cation counterion is one of an imidazolium, a pyrrolidininium, a piperidinium, a phosphonium, a pyridinium, a pyrrolinium, a sulfonium cation, or any other cation that provides the desired properties. In an embodiment, the conducting liquid is in the liquid phase between −20 degrees Celsius and 70 degrees Celsius. In an embodiment, the conducting liquid has a transmittance of at least 50% (including, in some embodiments, at least 85%) over a thickness of 1 mm for electromagnetic waves having a wavelength between 1400 nm and 1550 nm. In an embodiment, the cation counterion is an imidazolium cation having the general formula

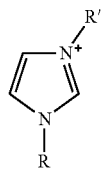

wherein, R is hydrogen or an alkyl group, and R' is hydrogen or any organyl group. In an embodiment, the imidazolium cation is one of 1-ethyl-3-methylimidazolium cation, 1-allyl-3-methylimidazolium, 1-benzyl-3-methylimidazolium, 1-butyl-3-methylimidazolium, 1-hexyl-3-methylimidazolium. In an embodiment, the imidazolium cation is one of 1-ethyl-3-methylimidazolium cation, 1-allyl-3-methylimidazolium, 1-benzyl-3-methylimidazolium, 1-butyl-3-methylimidazolium, 1-hexyl-3-methylimidazolium. In an embodiment, the cation counterion is a pyrrolidininium cation having the general formula

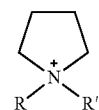

wherein R is hydrogen or an alkyl group, and R' is hydrogen or any organyl group. In an embodiment, the pyrrolidininium cation is one of N-ethyl-N-methylpyrrolidinium cation, 1-butyl-1-methylpyrrolidinium cation. In an embodiment, the pyrrolidininium cation is N-ethyl-N-methylpyrrolidinium cation. In an embodiment, the conducting liquid comprises a mixture of one or more of the aforementioned ionic compounds and another liquid, wherein the one or more of the aforementioned ionic compounds is at least 50% by weight of the conducting liquid, at least 60% by weight of the conducting liquid, at least 70% by weight of the conducting liquid, at least 80% by weight of the conducting liquid, at least 90% by weight of the conducting liquid, or at least 99% by weight of the conducting liquid.

According to a third aspect of the present disclosure, a liquid lens comprises: a lens body forming a cavity that retains a conducting liquid and an insulating liquid, the conducting liquid being immiscible with the insulating liquid and forming an interface between the conducting liquid and the insulating liquid; the conducting liquid comprising an ionic compound of either a dicyanamide anion and a cation counterion, or a tricyanomethanide anion and a cation counterion, the dicyanamide anion having the general formula

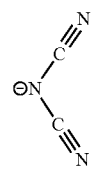

the tricyanomethanide anion having the general formula

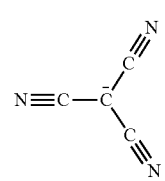

and the cation counterion is one of an imidazolium, a pyrrolidininium, a piperidinium, a phosphonium, a pyridinium, a pyrrolinium or a sulfonium cation. In an embodiment, the conducting liquid is in a liquid phase between −20 degrees Celsius and 70 degrees Celsius. In an embodiment, the conducting liquid has a density and the insulating liquid has a density, and the density of the conducting liquid is within 0.10 g/cm³ at 20 degrees Celsius of the density of the insulating liquid. In an embodiment, the cation counterion is one of 1-ethyl-3-methylimidazolium cation, 1-allyl-3-methylimidazolium cation, 1-benzyl-3-methylimidazolium cation, 1-butyl-3-methylimidazolium cation, 1-hexyl-3-methylimidazolium cation, 1-ethyl-3-methylimidazolium cation, N-ethyl-N-methylpyrrolidinium cation, 1-butyl-1-methylpyrrolidinium cation, or trihexyltetradecylphosphonium cation. In an embodiment, the ionic compound of the conducting liquid is N-methyl-N-ethylpyrrolidinium dicyanamide. In an embodiment, the ionic compound of the conducting liquid is 1-ethyl-3-methylimidazolium dicyanamide. In an embodiment, the ionic compound of the conducting liquid is 1-butyl-1-methylpyrrolidinium tricyanomethanide. In an embodiment, the ionic compound of the conducting liquid is 1-ethyl-3-methylimidazolium tricyanomethanide. In an embodiment, the conducting liquid has a transmittance of at least 50% (including, in some embodiments, at least 80%, and in some embodiments, at least 85%) over a thickness of 1 mm for electromagnetic waves having a wavelength between 1400 nm and 1550 nm.

Additional features and advantages will be set forth in the detailed description which follows, and in part will be readily apparent to those skilled in the art from that description or recognized by practicing the embodiments as described herein, including the detailed description and the claims, which follow.

It is to be understood that both the foregoing general description and the following detailed description are merely exemplary, and are intended to provide an overview or framework to understanding the nature and character of the claims.

BRIEF DESCRIPTION OF THE DRAWINGS

FIG. 2A is a perspective cross-sectional view of other embodiments of a liquid lens that can utilize the conducting liquid and insulating liquid, which remain separated at an interface, and the interface operates as a lens to manipulate (such as focus) electromagnetic waves;

FIG. 2B is an elevational cross-sectional view of the liquid lens embodiments of FIG. 2A with the conducting liquid and insulating liquid disposed therein and separated at the interface, and the interface operates as a lens to manipulate (such as focus) electromagnetic waves;

DETAILED DESCRIPTION

Structure of an Exemplary Liquid Lens

Figure 1:
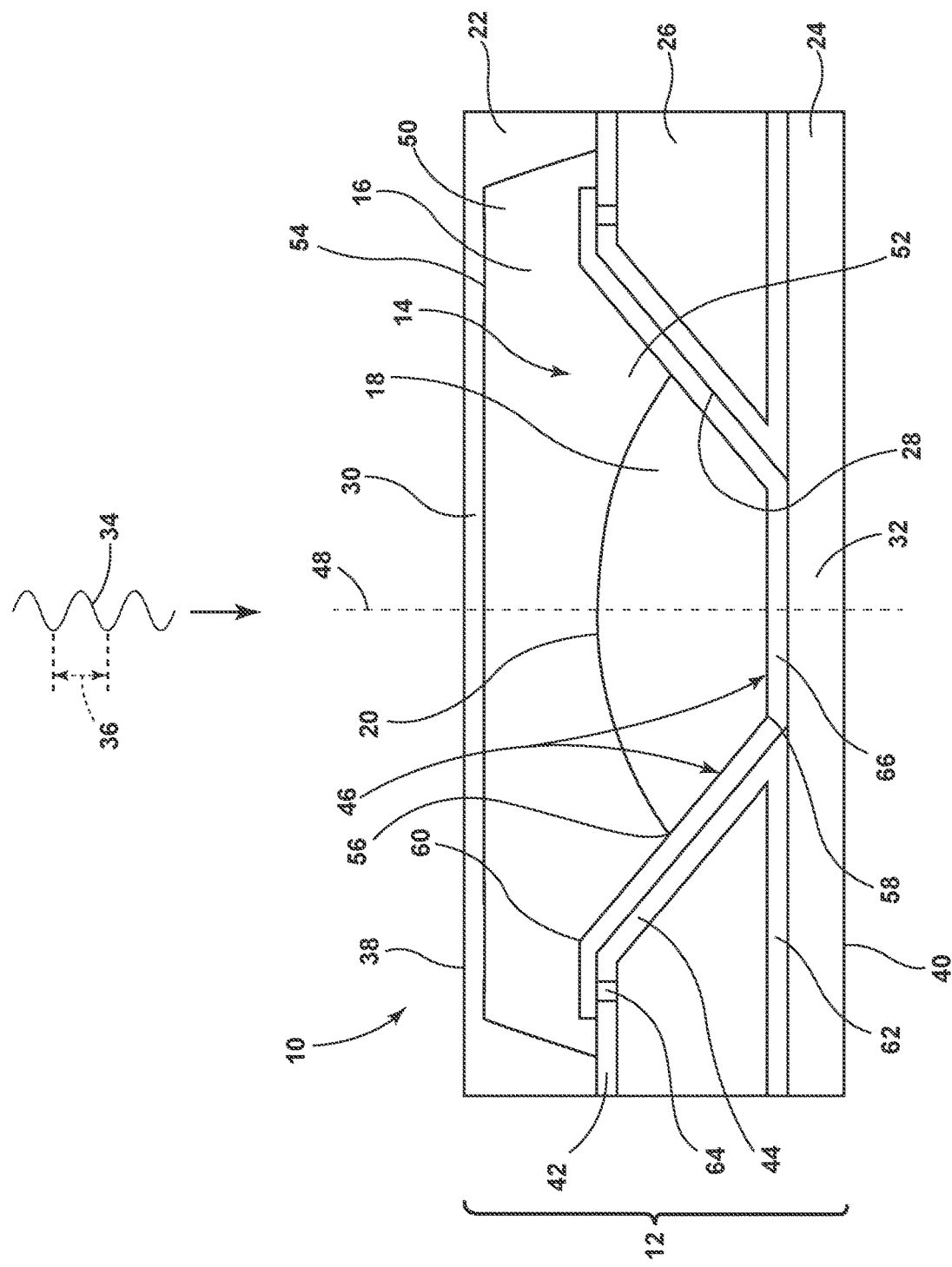
FIG. 1 is an elevation cross-sectional view of some embodiments of a liquid lens that can utilize a conducting liquid and an insulating liquid, which remain separated at an interface, and the interface operates as a lens to manipulate (such as, focus) electromagnetic waves.

Referring now to FIG. 1, a simplified cross-sectional view of an exemplary liquid lens 10 is illustrated. The liquid lens 10 includes a lens body 12. The lens body 12 forms a cavity 14. The cavity 14 retains a conducting liquid 16 and an insulating liquid 18. The conducting liquid 16 and the insulating liquid 18 are immiscible and thus an interface 20 is formed between the conducting liquid 16 and the insulating liquid 18. Because the conducting liquid 16 and the insulating liquid 18 have different indices of refraction, the interface 20 operates as a lens.

In some embodiments, a plurality of layers cooperatively form the lens body 12 and thus the cavity 14, within which the conducting liquid 16 and the insulating liquid 18 are disposed. For example, in the illustrated embodiment, the lens body 12 comprises a first outer layer 22, and a second outer layer 24, and an intermediate layer 26 disposed between the first outer layer 22 and the second outer layer 24. The intermediate layer 26 may comprise a bore 28 formed therethrough to define a portion of the cavity 14. A first window 30 is disposed at the first outer layer 22. A second window 32 is disposed at the second outer layer 24.

The first window 30 and the second window 32 are sufficiently transparent to enable passage of the electromagnetic waves 34 having the wavelength 36 desired to be sensed through the liquid lens 10. Incident electromagnetic waves 34 having a wavelength 36 enter the liquid lens 10 through the first window 30, are manipulated at the interface 20 between the conducting liquid 16 and the insulating liquid 18, and then exit the liquid lens 10 through the second window 32. In some embodiments, the entirety of the first outer layer 22 and/or the second outer layer 24 are sufficiently transparent to the wavelength 36 of the electromagnetic waves 34 desired to be sensed. Because electromagnetic waves 34 can pass through the bore 28 in the intermediate layer 26, the intermediate layer 26 need not be transparent to the wavelength 36 of the electromagnetic waves 34 desired to be sensed but can be.

In some embodiments, outer surfaces 38, 40 of the first outer layer 22 and/or the second outer layer 24, respectively, are substantially planar. Thus, even though the liquid lens 10 functions as a lens (e.g., by refracting electromagnetic waves 34 passing through interface 20), the outer surfaces 38, 40 of the liquid lens 10 can be flat as opposed to being curved like the outer surfaces of some fixed lenses. In other embodiments, the outer surfaces 38, 40 of the first outer layer 22 and/or the second outer layer 24, respectively, can be curved (e.g., concave or convex). Thus, the liquid lens 10 may comprise an integrated fixed lens.

The liquid lens 10 further includes a common electrode 42 in electrical communication with the conducting liquid 16. In addition, the liquid lens 10 includes one or more driving electrode(s) 44, which can be disposed near or at a sidewall of the cavity 14 and insulated from the conducting liquid 16 and the insulating liquid 18. Different voltages can be supplied to the common electrode 42 and the driving electrode(s) 44 to change the shape of the interface 20 as described herein via a phenomenon referred to as electrowetting. In other words, the voltage can be manipulated to increase or decrease the wettability of a surface 46 of the cavity 14 with respect to the conducting liquid 16 and alter the shape or position of the interface 20. In some embodiments, the voltage is manipulated to change the shape of the interface 20, which changes the focal length or focus of liquid lens 10. For example, such a change of focal length can enable the liquid lens 10 to perform an autofocus function. In other embodiments, the voltage is manipulated to change the position of (such as tilt) the interface 20 relative to an optical axis 48 of the liquid lens 10. For example, such tilting of the interface 20 can enable the liquid lens 10 to perform an optical image stabilization (OIS) function. Adjusting the interface 20 can be achieved without physically moving the lens body 12 relative to an image sensor, a fixed lens or lens stack, a housing, or other components of a device in which the liquid lens 10 can be incorporated. To provide a wide range of focal distances and tilt angles, a significant difference in the optical index between the conducting liquid 16 and the insulating liquid 18 can be beneficial. In some embodiments, the conducting liquid 16 and the insulating liquid 18 have substantially the same density, which can help to avoid changes in the shape or tilt of the interface 20 as a result of changing the physical orientation of lens body 12 (e.g., as a result of gravitational forces).

In some embodiments of the liquid lens 10, the cavity 14 includes a headspace 50 and a base portion 52. For example, the bore 28 in the intermediate layer 26 of liquid lens 10 may define the base portion 52 of the cavity 14. A recess 54 in the first outer layer 22 of the liquid lens 10 may define the headspace 50 of the cavity 14, and the headspace 50 may be disposed outside of the bore 28 in the intermediate layer 26 as described herein. In the illustrated embodiment, at least a portion of the conducting liquid 16 is disposed in the headspace 50 of the cavity 14, and the insulating liquid 18 is disposed within the base portion 52 of the cavity 14. Substantially all or a portion of the insulating liquid 18 may be disposed within the base portion 52 of the cavity 14. In some embodiments, a perimeter 56 of the interface 20 contacts the surface 46 of the cavity 14 within the base portion 52 of the cavity 14.

In the illustrated embodiment, the cavity 14 (more specifically, the base portion 52 of the cavity 14) is tapered such that a cross-sectional area of the cavity 14 decreases along the optical axis 48 in a direction from the first window 30 toward the second window 32. For example, the base portion 52 of the cavity 14 has a narrow end 58 and a wide end 60. The terms "narrow" and "wide" are relative terms, meaning the narrow end 58 is narrower than the wide end 60. Such a tapering of the cavity 14 can help to maintain alignment of the interface 20 between the conducting liquid 16 and the insulating liquid 18 along the optical axis 48. In other embodiments, the cavity 14 can be tapered such that the cross-sectional area of the cavity 14 increases along the optical axis 48 in the direction from the first window 30 toward the second window 32, or non-tapered such that the cross-sectional area of the cavity 14 remains substantially constant along the optical axis 48.

In the illustrated embodiment, the liquid lens 10 further includes a conductive layer 62. At least a portion of the conductive layer 62 faces toward the cavity 14. The conductive layer 62 can be a conductive coating applied to the intermediate layer 26 before bonding the first outer layer 22 and/or the second outer layer 24 to the intermediate layer 26. The conductive layer 62 can comprise a metallic material, a conductive polymer material, another suitable conductive material, or a combination thereof. The conductive layer 62 can be formed from a single layer or a plurality of layers, some or all of which are conductive. In some embodiments, the conductive layer 62 defines the common electrode 42 and/or the driving electrode(s) 44. For example, the conductive layer 62 can be applied to substantially the entire outer surface of the intermediate layer 26 before bonding the first outer layer 22 and/or the second outer layer 24 to the intermediate layer 26. Following application of the conductive layer 62 to the intermediate layer 26, the conductive layer 62 may be segmented into various conductive elements (e.g., the common electrode 42 and/or the driving electrode 44). In some embodiments, the conductive layer 62 is segmented at a scribe 64 to isolate (e.g., electrically isolate) the common electrode 42 and the driving electrode 44 from each other. In some embodiments, the scribe 64 is a gap in the conductive layer 62. For example, the scribe 64 can be a gap with a width of about 5 µm, about 10 µm, about 15 µm, about 20 µm, about 25 µm, about 30 µm, about 35 µm, about 40 µm, about 45 µm, about 50 µm, or any ranges defined by the listed values.

In the illustrated embodiment, the liquid lens 10 further includes an insulating layer 66 disposed on the driving electrode 44 layer and facing the cavity 14. For example, to form the insulating layer 66, an insulating coating can be applied over the conductive layer 62 and the second window 32 after the second outer layer 24 and the intermediate layer 26 are bonded together but before the first outer layer 22 and the intermediate layer 26 are bonded. Thus, the insulating layer 66 covers both at least a portion of the conductive layer 62 at the cavity 14 and the second window 32. The insulating layer 66 is sufficiently transparent to the wavelength 36 of the electromagnetic waves 34 intended to pass through the liquid lens 10 for sensing. In other embodiments, to form the insulating layer 66, an insulating coating is applied to the intermediate layer 26 before bonding the first outer layer 22 and/or the second outer layer 24 to the intermediate layer 26.

In the illustrated embodiment of the liquid lens 10, the insulating layer 66 covers a portion of the driving electrode(s) 44 that would otherwise be exposed to the cavity 14, to insulate the conducting liquid 16 and the insulating liquid 18 from the driving electrode(s) 44. However, in the illustrated embodiment, the insulating layer 66 does not cover at least a portion of the common electrode 42 exposed to the cavity 14. Thus, the common electrode 42 is in electrical communication with the conducting liquid 16.

Structure of Another Exemplary Lens

Referring now to FIGS. 2A and 2B, a simplified cross-sectional view of another exemplary liquid lens 200 is illustrated. The liquid lens 200 comprises a lens body 201 including a cap portion 202, a gasket 204, a base portion 206, a window 210, and a window 238. The lens body 201 forms a cavity 213. The cavity 213 retains the conducting liquid 16 and the insulating liquid 18.

The cap portion 202 is placed over the base portion 206 but separated from it by the gasket 204. The cap portion 202 comprises a metal cap 208 formed from a thin sheet of conducting metal, to which the disc shaped glass window 210 is sealed, for example, by a seal 212 formed by glue. The cap has a circular opening 214 allowing electromagnetic waves 34 to pass through to the glass window 210. The circular opening 214 is centered on the optical axis A of the liquid lens 200, and is on a plane perpendicular to the optical axis Δ.

Moving outwardly from the optical axis, the metal cap 208 comprises an annular flat portion 216 surrounding the opening 214 and being preferably perpendicular to the optical axis Δ. A first part of the inner surface of the portion 216 contacts the outer surface of the window 210, and a radially outer part of the inner surface of the portion 216 contacts with the outer edge of the window 210 and the seal 212. The outer edge of the portion 216 is curved to form an edge 218 that extends approximately at a right-angle, parallel to the optical axis Δ and that extends from the portion 216 toward the base portion 206. The edge 218 also preferably contacts with the seal 212. According to this embodiment, from edge 218, a substantially "S" shaped (e.g., undulating) portion 220 extends away from the optical axis Δ, linking the edge 218 to a further annular flat portion 222 that preferably extends at least substantially perpendicular to the optical axis Δ. This "S" shaped portion 220 is designed to allow some movement of the window 210 when pressure is exerted by fluids inside the liquid lens 200, but only movement in a direction parallel to the optical axis Δ.

A right-angled bend from the portion 222 links to an annular rim portion 224 extending at least substantially parallel to the optical axis Δ, which forms the outer rim of the liquid lens 200, surrounding the gasket 204 and the base portion 206. The end part of the portion 224, which is the outer edge of the metal sheet forming the metal cap 208, is preferably inwardly curved at a region 226 toward the optical axis Δ by crimping, such that it holds the gasket 204 and the base portion 206 in place.

The gasket 204 can be formed of a polymer and can be annular and substantially "L" shaped in cross section, such that an outer surface of a first leg or limb 228 of the "L" lies in contact with and parallel to the inner surface of the annular flat portion 222 of the metal cap 208, and an outer surface of a second leg or limb 230 of the "L" lies in contact with and parallel to the inner surface of the rim portion 224 of the metal cap 208, thus increasing the contact surface. Other shapes for the gasket 204 are possible. For example, in some embodiments, the gasket 204 may comprise only the first limb 228. The inner surfaces of the first and second limbs 228, 230 contact surfaces of the base portion 206. A region 232 at the end of the second limb 230 is curved inwardly toward the optical axis Δ by pressure applied by the crimped region 226 of the metal cap 208 (thus becoming a curved portion 232), and the inner surface of the gasket 204 at this point applies pressure on a corner of the base portion 206, holding it in place. The end surface 234 of the first limb 228 faces the optical axis Δ, and is exposed to the inner chamber of the liquid lens 200.

The base portion 206 preferably comprises an annular electrode 236, formed of a conducting material, preferably a metal, to which the disc shaped glass window 238, positioned generally perpendicularly to the optical axis A, is adhered and sealed by a seal 240, e.g., a glue or adhesive. An opening 242 is formed in the annular electrode 236, centered on the optical axis Δ, to allow light to pass through the glass window 238, to or from the liquid lens 200. The glass window 238 is positioned on the outside of the opening 242. The annular electrode 236 is molded or machined in a ring shape having a number of surfaces that are preferably rotationally symmetrical with respect to the optical axis Δ, which will now be described in more detail.

An inner edge 244 of the annular electrode 236 surrounding the opening 242 is preferably an inclined surface, for example, at approximately 45 degrees to the optical axis Δ, facing up into the liquid lens 200. Adjacent to and surrounding the inner edge 244 is an annular flat portion 246, also generally perpendicular to the optical axis Δ, and adjacent to this is a further inclined edge 248, again facing into the liquid lens 200 and being approximately parallel to the inner edge 244. Adjacent to the inclined edge 248 and surrounding it is an annular flat surface 250, an inner part of which is exposed to the inner chamber of the liquid lens 200, and an outer part of which provides a first contact surface in contact with the inner surface of the limb 228 of the gasket 204. Adjacent to the surface 250 is an edge surface 252, generally parallel to the optical axis A, which preferably provides a second contact surface in contact with the inner surface of the limb 230 of the gasket 204. An annular flat outer surface 254 adjacent to the edge surface 252 faces out from the liquid lens 200 and extends back toward the optical axis Δ. The generally right-angled corner between the edge surface 252 and the outer surface 254 is the corner that preferably contacts the inner region of the gasket 204, that is curved by the crimped region 226 of the metal cap 208. A further surface 256 adjacent to the outer surface 254 extends out from the liquid lens 200, generally parallel to the optical axis Δ, and adjacent to the surface 256 and an annular surface 258 that is generally perpendicular to the optical axis A extends inwardly toward the optical axis Δ. A radially inwardly facing surface 260 extends generally parallel to the optical axis A adjacent to the annular surface 258 and extends back toward the inner chamber of the liquid lens 200. A surface 260 is adjacent to an annular flat surface 262, also generally perpendicular to the optical axis Δ, which terminates at the inner edge 244 of the annular electrode 236. A radially inner part of the annular flat surface 262 contacts the glass window 238, and a radially outer part of the annular flat surface 262 contacts with the seal 240, which holds the window 238 in place.

The annular electrode 236 preferably comprises contact surfaces 260, 262 for the receiving window 238, the inner edge 244 for receiving the insulating liquid 18, the first and second contact surfaces 250, 252 for contacting with the inner surfaces of the gasket 204, and a corner between the surfaces 252 and 254 for contacting with the curved portion 232 of the gasket 204, thereby holding the annular electrode 236 in place.

Although not shown in FIG. 2A, but shown in FIG. 2B, the liquid lens 200 contains the conducting liquid 16 and the insulating liquid 18 within the cavity 213 formed between the windows 210 and 238. The insulating liquid 18, which can be a dielectric, is positioned covering the opening 242 of the annular electrode 236 on the surface of the glass window 238. The edges of the insulating liquid 18 preferably fall within a part of the inner edge 244 of the annular electrode 236. The conducting liquid 16 fills the remaining volume of the cavity 213. Neither of the conducting liquid 16 or the insulating liquid 18 make direct contact with the exposed surfaces of the annular electrode 236 which have been covered with an insulating layer, as will be explained in more detail below. The conducting liquid 16 of the "S" shaped region 220 of the metal cap 208, which is exposed to the cavity 213, makes electrical contact therewith.

In operation, a voltage, which is preferably oscillating, is applied between the annular electrode 236 and the metal cap 208, the metal cap 208 functioning as the second electrode and making contact with the conducting liquid 16. This voltage alters the curvature of the interface 20 between the conducting liquid 16 and the insulating liquid 18, due to the electrowetting effect which increases the wettability of the inner edge 244 by water. The conducting liquid 16 and the insulating liquid 18 have different refractive indices, such that the electromagnetic waves 34 are refracted at the interface 20. The electromagnetic waves 34 pass through the windows 210 and 238, passing through the interface 20 between the conducting liquid 16 and the insulating liquid 18.

An insulation layer, which is, for example, a polymer, is applied to the top and sides of the base portion 206, that is, to surfaces 252, 250, 248, 246, 244 and across the surface of the window 238, to ensure that electrowetting is effective. A soft polymer coating 400 can be applied to the exposed inner surfaces of the metal cap 208 that contact the gasket 204, in other words over the inner surfaces of portions 224 and 222, and on at least a portion of the inner part of the "S" shaped portion 220. The gasket 204 can be coated on both outer and inner surfaces with soft polymer coatings 402 and 404, respectively. These are the regions in contact with the metal cap 208 and the base portion 206, respectively. A polymer coating 406 can be applied to the outer edge surface 252 and the top surface 250 of the annular electrode 236, over the insulation layer (e.g., the surfaces in contact with the gasket 204).

The liquid lens 10 and the liquid lens 200 are examples to provide context for the novel conducting liquids 16 described herein and are not meant to limit the applicability of the novel conducting liquids 16 to liquid lenses having a different structure and makeup. The novel conducting liquids 16 described herein can be advantageously utilized in any liquid lens structure.

The Insulating Layer

The insulating layer 66 of the liquid lens 10, and the insulation layer applied to the top and sides of the base portion 206, that is, to surfaces 252, 250, 248, 246, 244, and across the surface of the window 238 of the liquid lens 200, can be, for example:

Silicone polymers PDSM;
Amorphous fluoro polymers, such as Teflon® AF 1600 and AF 1601 from DuPont;
Poly(arylene ethers);
Fluorinated poly(arylene ethers);
para-Xylylene linear polymers, fluorinated or not, such as parylenes, for example Parylene C, Parylene F or Parylene AF-4, Parylene VT-4, Parylene N or Parylene D;
Amorphous fluoro polymers, such as Cytop® from Asahi Glass Co;
Hyflon® polymer from Solvay;
Aromatic vinyl siloxane polymers, such as Divinylsiloxane-benzocyclobutene (DVS-BCB) polymer from Dow Chemical;
Diamond like carbon (DLC);
Poly(tetrafluoroethylene);
Polyethylene;
Polypropylene;
Fluoro ethylene propylene polymer;
Polynaphthalene;
Fluorinated polynaphthalene; and
Silicone-like polymeric films $SiO_xC_yH_z$.

The Insulating Liquid

In some embodiments, the insulating liquid 18 has a conductivity of less than $1 \times 10^{-8}$ S/m, less than $1 \times 10^{-10}$ S/m, or less than $1 \times 10^{-14}$ S/m. The insulating liquid 18 can be an organic or an inorganic compound or mixture thereof. Examples of such organic or inorganic compounds include hydrocarbons, Si-based monomers, oligomers, and polymers, and mixtures thereof. Other examples include Ge-based monomers, oligomers, and polymers, and Si—Ge-based monomers, oligomers, and polymers.

The hydrocarbon can be linear, branched, or contain one or more cyclic moiety(ies), whether saturated, unsaturated, or partially unsaturated. The hydrocarbon can have from about 8 to about 35 carbon atoms, or from 10 to about 20 carbon atoms. The hydrocarbon can have a boiling point above 100° C. The hydrocarbon can include a single hydrocarbon or petroleum distillate having a freezing point below −20° C.

The hydrocarbon can include one or more unsaturation(s) in the form of double and/or triple bond(s). However, more than 2 or 3 double or triple bonds can increase the risk of decomposition upon exposure to ultraviolet radiation. In some embodiments, the hydrocarbon does not contain any double or triple bonds, in which case the hydrocarbon can be referred to herein as an alkane.

The hydrocarbon may further comprise one or more heteroatoms, as substituents and/or as atoms or groups of atoms interrupting the hydrocarbon chain and/or ring. Such heteroatoms include, but are not limited to oxygen, sulfur, nitrogen, phosphor, halogens (mainly as fluorine, chlorine, bromine and/or iodine). Care should be taken that the presence of one or more heteroatom(s) does not impact the immiscibility of the two fluids.

The insulating liquid 18 can be a mixture that contains more than 99.8% of alkanes. Such a mixture can contain aromatic groups and/or unsaturated moieties in a ratio lower than 1 percent by weight of the insulating liquid 18 (e.g., lower than about 0.5 percent by weight). The mixture of alkanes may include impurities present as sub-product resulting from the preparation of the alkanes (e.g. when they are obtained by distillation process).

Some exemplary hydrocarbons for use in the insulating liquid 18 include: a linear or branched alkane, such as decane ($C_{10}H_{22}$), dodecane ($C_{12}H_{24}$), squalane ($C_{30}H_{62}$), and the like; an alkane comprising one or more rings, such as tert-butylcyclohexane ($C_{10}H_{20}$), and the like; a fused ring system, such as α-chloronaphthalene, α-bromonaphthalene, cis,trans-decahydronaphthalene ($C_{10}H_{18}$), and the like; a mixture of hydrocarbons, such as those available as Isopar® V, Isopar® P (from Exxon Mobil); and the like, and mixtures thereof.

As mentioned, the insulating liquid 18 can include silicon-based compounds. Such silicon-based compounds can include a siloxane of the formula Ia, Ib, or Ic:

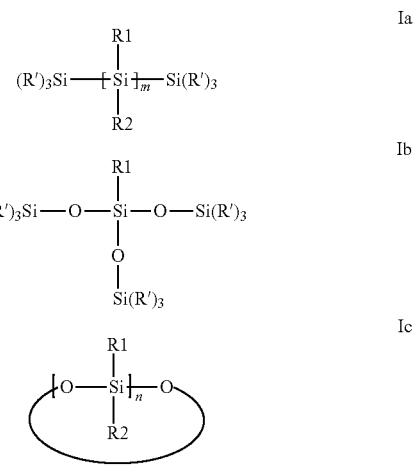

wherein each of R1, R2 and R' independently represents alkyl, (hetero)aryl, (hetero)arylalkyl, (hetero)arylalkenyl or (hetero)arylalkynyl and n is comprised between about 1 and 20, or between 1 and 10 (e.g., 1, 2, 3, 4 or 5) and with the caveat that n is greater than 2 in formula Ic.

Such silicon-based compounds can include a silane of formula II:

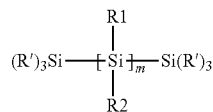

II wherein R1, R2 and R' are as defined above and m is comprised between about 1 and about 20, or between about 1 and about 10 (e.g., 1, 2 or 3).

Such silicon-based compounds can include a monosilane of formula Ill:

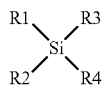

III wherein R1 and R2 are as defined above, and each of R3 and R4 independently represents alkyl, (hetero)aryl, (hetero)arylalkyl, (hetero)arylalkenyl or (hetero)arylalkynyl.

In the above formulae: (1) alkyl means a straight or branched alkyl radical having from about 1 to about 10 carbon atoms, or from about 1 to about 6 carbon atoms; alkyls can includes methyl, ethyl, n-propyl, iso-propyl; alkyl radical may be halogenated, for instance may comprise a 1,1,1-trifluoropropyl group; (2) (hetero)aryl means an aromatic or heteroaromatic radical containing from about 5 to about 12 atoms, forming at least one (e.g., one), aromatic and/or heteroaromatic ring, said ring(s) being optionally substituted by one or more halogens (e.g., 1, 2, 3 halogen atoms, such as fluorine, chlorine and/or bromine), and being optionally fused with one or more saturated, partially saturated or unsaturated ring system; (hetero)aryls can include phenyl, naphthyl, bicyclo[4.2.0]octatrienyl, optionally substituted with 1, 2 or 3 halogen atoms; (3) (hetero)arylalkyl is as defined above for each of the alkyl and (hetero)aryl radical; (hetero)arylalkyls can include benzyl, phenethyl, optionally substituted with 1, 2 or 3 halogen atoms; and (4) (hetero)arylalkenyl and (hetero)arylalkynyl correspond to radicals wherein the (hetero)aryl moiety is as defined above, and alkenyl and alkynyl represent a straight or branched alkyl radical, as defined above, further comprising one or more (e.g., one) double bond or one or more (e.g., one) triple bond, respectively.

Some exemplary silicon-based compounds for use in the insulating liquid 18 include hexamethyidisilane, diphenyldimethylsilane, chlorophenyltrimethylsilane, phenyltrimethyl-silane, phenethyltris(trimethylsiloxy)silane, phenyltris(trimethylsiloxy)silane, polydimethylsiloxane, tetraphenyltetramethyltrisiloxane, poly(3,3,3-trifluoropropylmethylsiloxane), 3,5,7-triphenylnonamethyl-pentasiloxane, 3,5-diphenyloctamethyltetrasiloxane, 1,1,5,5-tetraphenyl-1,3,3,5-tetramethyl-trisiloxane, hexamethylcyclotrisiloxane, and n-octyltris(trimethylsiloxy)silane.

The insulating liquid 18 can contain one or more germane (Ge)-based species. Example germane based compounds include hexamethyldigermane, hexaethyldigermane, diphenyldimethylgermane, 1-naphtyltriethylgermane, and phenyltrimethylgermane.

The insulating liquid 18 can include at least one Si- and/or Ge-based compound substituted by one or more phenyl groups and/or other groups like fluorinated or non-fluorinated alkyl (ethyl, n-propyl, n-butyl), linear or branched alkyls, chlorinated or brominated phenyl groups, benzyl groups, halogenated benzyl groups; or a mixture of Si- and/or Ge-based compounds wherein at least one compound is substituted by one or more phenyl groups and/or other groups like fluorinated or non-fluorinated alkyl (ethyl, n-propyl, n-butyl), linear or branched alkyls, chlorinated or brominated phenyl groups, benzyl groups, halogenated benzyl groups. Some specific examples include bis(nonafluorohexyl)tetramethyldisiloxane and (25-35% nonafluorohexylmethylsiloxane) (65-75% dimethylsiloxane) copolymer.

An example insulating liquid 18 includes dodecane, a nonafluorohexylmethylsiloxane/dimethylsiloxane copolymer, bis(nonafluorohexyl)tetramethyldisiloxane, and polydimethylsiloxane. Example percentages by weight of the total weight include: dodecane (12-30 percent); (25-35% non-afluorohexylmethylsiloxane) (65-75% dimethylsiloxane) copolymer (15-63 percent); bis(nonafluorohexyl)tetramethyldisiloxane (15-60 percent); and polydimethylsiloxane (10-30 percent). Another example insulating liquid 18 includes 1-naphtyltriethylgermane, n-octyltris(trimethylsiloxy)silane, and polyphenylether SANTOLIGHT SL-5267®. Another example insulating liquid 18 includes dodecane, (25-35% nonafluorohexylmethylsiloxane) (65-75% dimethylsiloxane) copolymer, bis(nonafluorohexyl)tetramethyldisiloxane, hexamethyldigermane, and hexaethyldigermane. Adjusting the percentages by weight of individual components of the insulating liquid 18 affects the density, viscosity, and refraction index of the insulating liquid 18.

Conducting Liquid

In some embodiments, the novel conducting liquid 16 of the present disclosure includes ionic compounds of one or more of the dicyanamide anion and the tricyanomethanide anion and a cation counterion. The dicyanamide anion is represented by the formula IV:

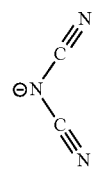

IV

The tricyanomethanide anion is represented by the formula V:

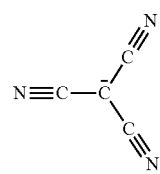

V

It has been discovered that ionic compounds that incorporate the dicyanamide anion or the tricyanomethanide anion with a cation counterion: (1) are more likely to have a melting point closer to −20 degrees Celsius or colder; (2) are more likely to have a density closer to 1.0 g/cm$^3$ at 20 degrees Celsius and thus are easier to pair with typically used insulating liquids 18; (3) are immiscible with typically used insulating liquids 18 despite the lack of hydroxyl groups; and (4) are more transparent to electromagnetic waves 34 having a wavelength 36 longer than the visible region than typically used conducting liquids 16 that contain hydroxyl groups.

Without wishing to be bound by theory, it is believed that one or more hydroxyl groups present in conventional conducting liquid are at least partially responsible for the immiscibility of the conducting liquid with typical insulating liquid, but also absorb electromagnetic waves having wavelength of 1400 nm or greater. By absorbing electromagnetic waves having wavelength of 1400 nm or greater, those hydroxyl groups can prevent the conducting liquid from transmitting a sufficient percentage of the incident electromagnetic waves having wavelength of 1400 nm or greater through a liquid lens to be sensed and processed. Thus, the one or more hydroxyl groups can preclude liquid lenses using conventional conducting liquids from being used in applications intended to sense electromagnetic waves having a wavelength of 1400 nm or greater. In some embodiments, the ionic compounds disclosed herein can have few or no hydroxyl groups, which can help to address the shortcomings of conventional conducting liquids for use in applications involving electromagnetic waves having wavelengths of 1400 nm or greater.

An example application that can involve sensing of electromagnetic waves having a wavelength of 1400 nm or greater is optical communication, which can involve sensing of electromagnetic waves that have a typical wavelength of 1550 nm. In addition, some lidar surveying methods can involve sensing electromagnetic waves having a wavelength of 1550 nm. As another example, short-wave infrared (SWIR) imaging can involve sensing electromagnetic waves having a wavelength between 900 nm and 1700 nm (e.g., utilizing InGaAs sensors).

In some embodiments, the conducting liquid and the insulating liquid have properties that help to make them compatible for use in liquid lens applications. For example, the densities of the conducting liquid and the insulating liquid can be the same or substantially the same (e.g., differ by not more than about 3.10$^{-3}$ g/cm$^3$ at 20 degrees Celsius). In addition, the kinematic viscosities of the conducting liquid and the insulating liquid can be sufficiently low and/or the same or substantially the same (e.g., within 0 cSt and ±5 cSt of each other over the temperature range of intended use). Moreover, the melting point of the conducting liquid and the insulating liquid can be sufficiently low (e.g., −20 degrees Celsius or less, such as −40 degrees Celsius). In some applications, the conducting liquid and the insulating liquid can be in the liquid phase over a temperature range from −20 degrees Celsius to 70 degrees Celsius (e.g., at a standard pressure, such as 1 atm). In other applications, the conducting liquid and the insulating liquid can be in the liquid phase over a temperature range from −40 degree Celsius to 85 degrees Celsius (e.g., at a standard pressure, such as 1 atm).

Both the dicyanamide anion and the tricyanomethanide anion can be matched with many possible cation counterions to form the ionic compound used as or in the conducting liquid 16. Exemplary cation counterions to pair with the dicyanamide anion or the tricyanomethanide anion include imidazolium, pyrrolidininium, piperidinium, phosphonium, pyridinium, pyrrolinium and sulfonium-based cations.

The imidazolium cation has the general formula VI below,

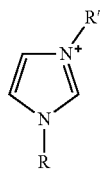

VI wherein R is hydrogen or an alkyl group, and R' is hydrogen or any organyl group, with the caveat that the number of hydroxyl groups in the organyl group is preferably 0. In some embodiments of an imidazolium cation, R' is a methyl group and R is an ethyl group, and the cation is referred to as 1-ethyl-3-methylimidazolium cation. The ionic compound 1-ethyl-3-methylimidazolium dicyanamide has a density of 1.101 g/cm$^3$ at 26 degrees Celsius, a viscosity of 16.8 mPa*s at 21 degrees Celsius, a melting point of −21 degrees Celsius, and a refractive index (589 nm) of 1.516. The ionic compound 1-ethyl-3-methylimidazolium tricyanomethanide has a density of 1.08 g/cm$^3$ at 25 degrees Celsius, a viscosity of 14.0 cP at 25 degrees Celsius, a melting point of −11° C., and a refractive index (589 nm) of 1.512. The densities of both 1-ethyl-3-methylimidazolium dicyanamide and 1-ethyl-3-methylimidazolium tricyanomethanide are suitable to be matched with typical components of the insulating liquid 18. Another imidazolium cation appropriate for some embodiments is 1-allyl-3-methylimidazolium cation. The ionic compound 1-allyl-3-methylimidazolium dicyanamide has a density of 1.11 g/cm$^3$ at 24 degrees Celsius, a viscosity of 16 mPa*s at 18 degrees Celsius, and a melting point below room temperature. Another imidazolium cation appropriate for some embodiments is 1-benzyl-3-methylimidazolium cation. The ionic compound 1-benzyl-3-methylimidazolium dicyanamide has a density of 1.16 g/cm$^3$ at 24 degrees Celsius, a viscosity of 78.5 mPa*s at 25 degrees Celsius, and a melting point below room temperature. Another imidazolium cation appropriate for some embodiments is 1-butyl-3-methylimidazolium cation. The ionic compound 1-butyl-3-methylimidazolium dicyanamide has a density of 1.06 g/cm$^3$ at 25 degrees Celsius, a viscosity of 28 mPa*s at 25 degrees Celsius, and a melting point below 0 degrees Celsius. The ionic compound 1-butyl-3-methylimidazolium tricyanomethanide has a density of 1.05 g/cm$^3$ at 25 degrees Celsius and a viscosity of 27.3 cP at 25 degrees Celsius. Another imidazolium cation appropriate for some embodiments is 1-hexyl-3-methylimidazolium cation. The ionic compound 1-hexyl-3-methylimidazolium tricyanomethanide has a density of 1.02 g/cm$^3$ at 24 degrees Celsius, a viscosity of 39.2 cP at 25 degrees Celsius, and a melting point below room temperature.

The pyrrolidininium cation has the general formula VII below,

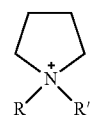

VII wherein R is hydrogen or an alkyl group, and R' is hydrogen or any organyl group, with the caveat that the number of hydroxyl groups in the organyl group is preferably 0. In some embodiments of a pyrrolidininium cation, R is an ethyl group and R' is a methyl group, and the cation is referred to as N-ethyl-N-methylpyrrolidinium cation. The ionic compound N-ethyl-N-methylpyrrolidinium dicyanamide can be a suitable ionic compound for use as or in the conducting liquid 16 in some embodiments. The ionic compound N-ethyl-N-methylpyrrolidinium tricyanomethanide can be a suitable ionic compound for use as or in the conducting liquid 16 in some embodiments.

Another pyrrolidininium cation appropriate for some embodiments is 1-butyl-1-methylpyrrolidinium cation. The ionic compound 1-butyl-1-methylpyrrolidinium dicyanamide has a density of 1.02 g/cm$^3$ at 20 degrees Celsius, a viscosity of 46 mPa*s at 20 degrees Celsius, and a melting point of −55 degrees Celsius. The ionic compound 1-butyl-1-methylpyrrolidinium tricyanomethanide has a density of 1.01 g/cm$^3$ at 25 degrees Celsius, a viscosity of 26.9 cP at 25 degrees Celsius. The densities of both 1-ethyl-3-methylimidazolium dicyanamide and 1-ethyl-3-methylimidazolium tricyanomethanide are suitable to be matched with typical components of the insulating liquid 18. The melting point well below −20° C. of 1-butyl-1-methylpyrrolidinium dicyanamide makes that ionic compound suitable to be the conducting liquid 16 in many applications for the liquid lens 10.

The piperidinium cation has the general formula VIII below,

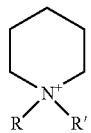

VIII wherein R is hydrogen or an organyl group, and R' is hydrogen or an organyl group, in which the number of hydroxyl groups in the organyl group can be 0.

The phosphonium cation has the general formula IX below.

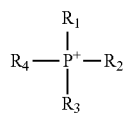

IX wherein, R1, R2, R3, R4 can each individually be hydrogen or any organyl group, in which the number of hydroxyl groups in the organyl group can be 0. A phosphonium cation appropriate for some embodiments is trihexyltetradecylphosphonium cation. The ionic compound trihexyltetradecylphosphonium dicyanamide has a density of 0.90 g/cm$^3$ at 28 degrees Celsius, a viscosity of 361 mPa*s at 25 degrees Celsius, and a melting point below room temperature. The ionic compound trihexyltetradecylphosphonium tricyanomethanide is also commercially available.

The pyridinium cation has the general formula X below,

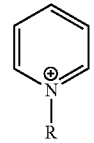

X wherein, R can be hydrogen or any organyl group, in which the number of hydroxyl groups in the organyl group can be 0.

The pyrrolinium cation has the general formula XI below,

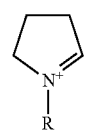

XI wherein, R can be hydrogen or any organyl group, in which the number of hydroxyl groups in the organyl group can be 0.

The sulfonium cation has the general formula XII below,

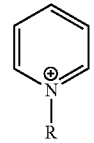

XII wherein, $R^1$, $R^2$, and $R^3$ can be hydrogen or any organyl group, in which the number of hydroxyl groups in the organyl group can be 0.

The conducting liquid 16 can further include a solvent. However, the total w/w concentration of hydroxyl containing substances in the conducting liquid 16 should be below 20%, below 10%, below 5%, or below 1%. Exemplary polar solvents that do not include hydroxyl groups include dimethylsulfoxide, dimethylformamide, dialkyl ethylene glycol ethers, dialkyl propylene glycol ethers, carbonates, and lactames.

Figure 3:
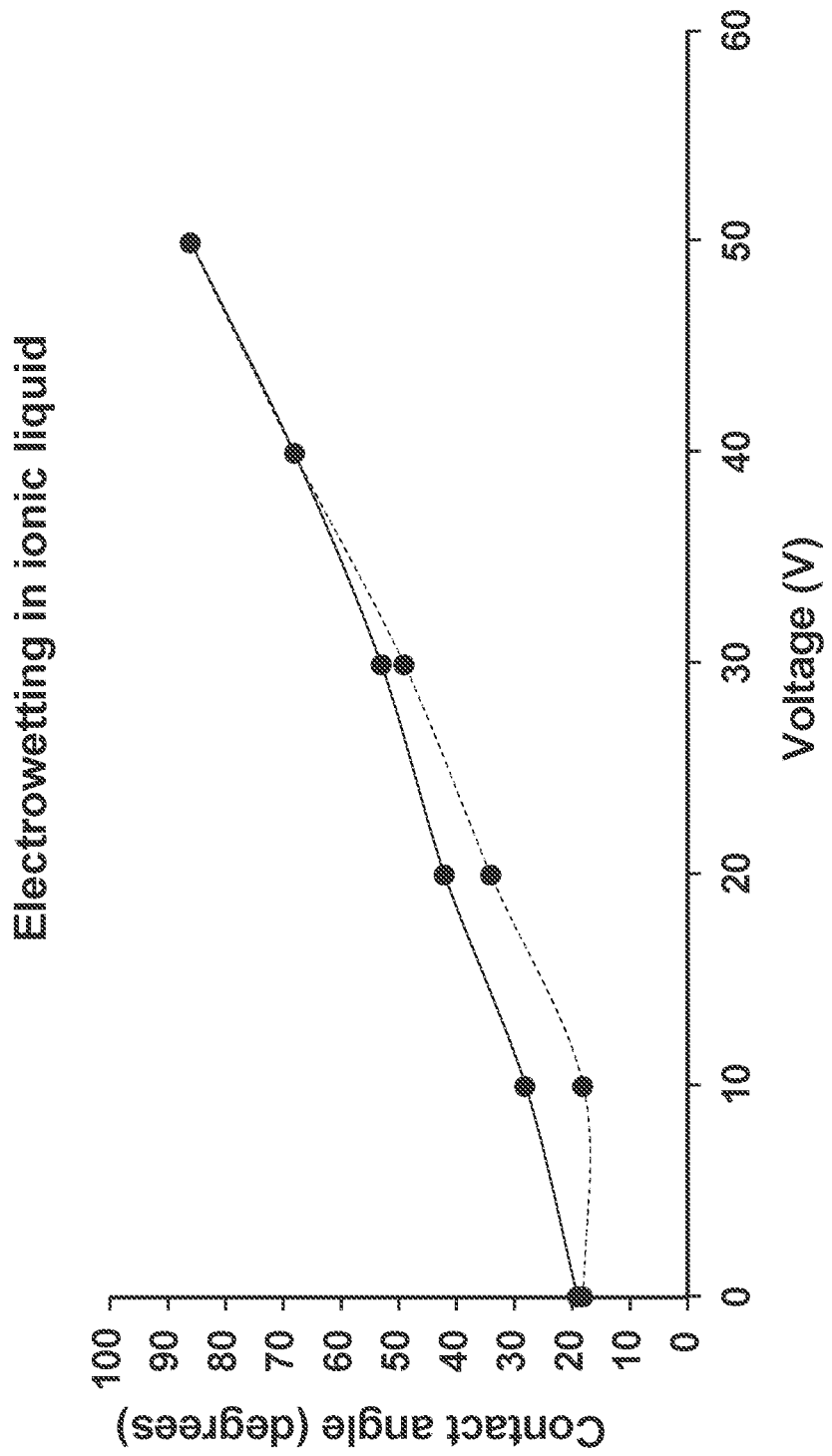
FIG. 3 is a graph of the contact angle as a function of applied voltage for 1-ethyl-3-methylimidazolium dicyanamide (as the conducting liquid) with diphenyldimethylgermane (as the insulating liquid) for (a) while the voltage is increasing, and (b) while the voltage is decreasing.

Referring now to FIG. 3, an electrowetting experiment was performed to determine contact angle as a function of voltage for 1-ethyl-3-methylimidazolium dicyanamide (as the conducting liquid 16) with diphenyldimethylgermane (as the insulating liquid 18). The graph shows a low electrowetting hysteresis in voltage ranges above 30 volts.

Figure 4A:
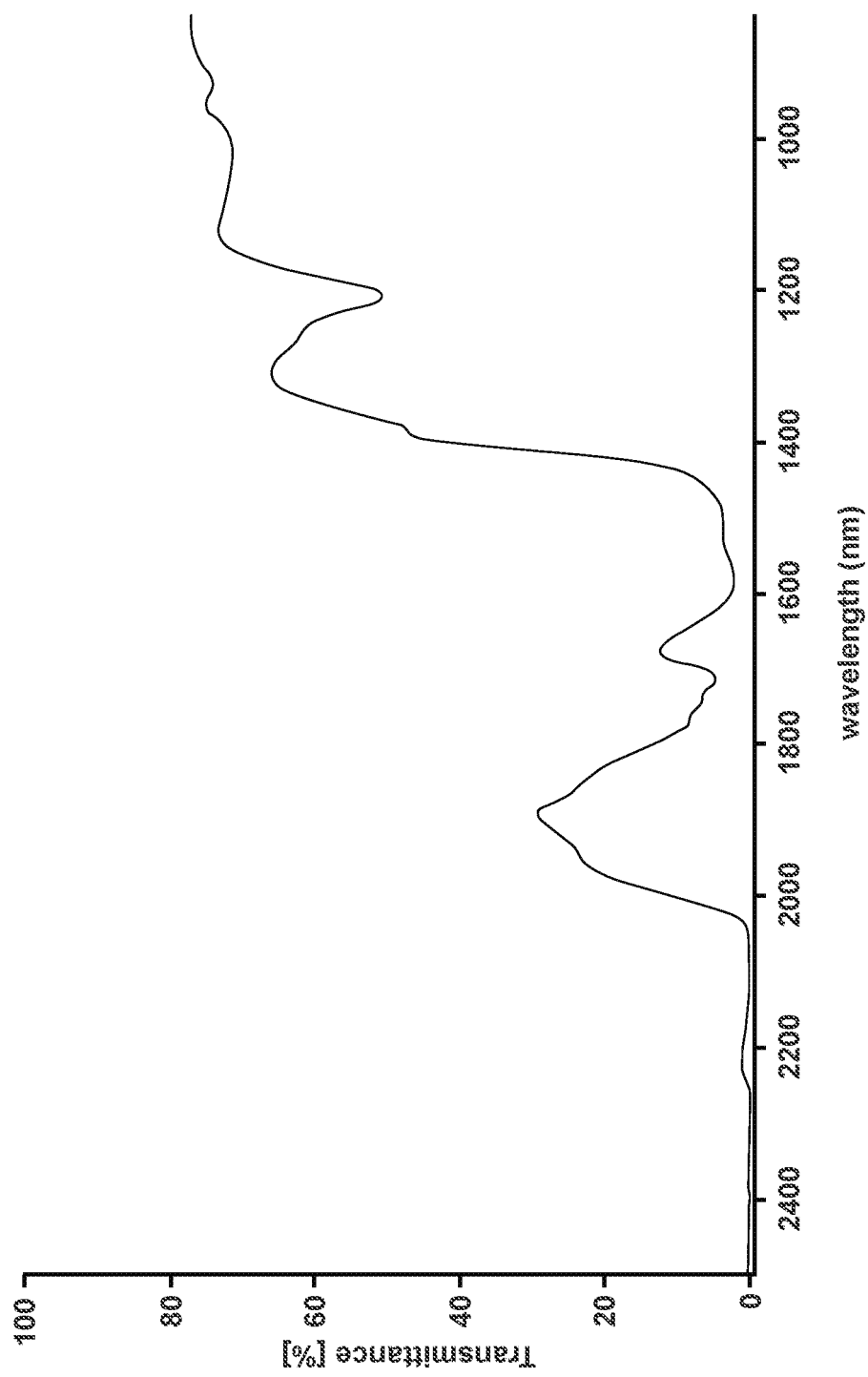
FIG. 4A is a graph of the percentage transmittance of incident electromagnetic waves through ethylene glycol as a function of the wavelength of the electromagnetic waves.
Figure 4B:
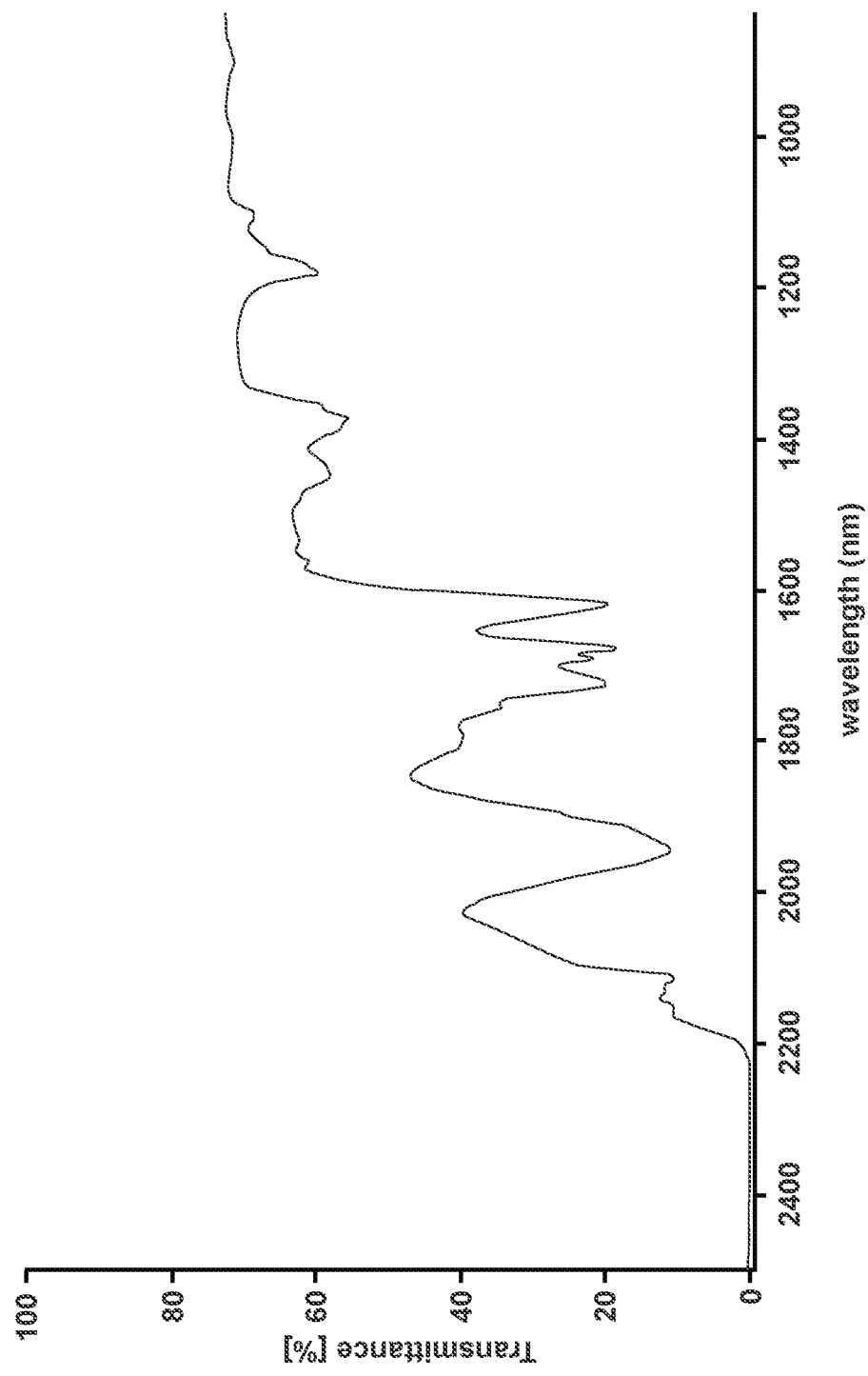
FIG. 4B is a graph of the percentage transmittance of incident electromagnetic waves through 1-ethyl-3-methylimidazolium dicyanamide as a function of the wavelength of the electromagnetic waves.

Referring now to FIGS. 4A and 4B, experiments were performed to determine the percentage transmittance of incident electromagnetic waves 34 as a function of the wavelength 36 of the electromagnetic waves 34 for both (a) 1-ethyl-3-methylimidazolium dicyanamide; and (b) ethylene glycol. The results for ethylene glycol are illustrated at FIG. 4A. The results for 1-ethyl-3-methylimidazolium dicyanamide are illustrated at FIG. 4B. In both experiments, the thickness of the liquid to which the incident electromagnetic waves 34 were directed was 1 mm. The results of the experiments demonstrate that 1-ethyl-3-methylimidazolium dicyanamide generally has a higher transmissivity (percentage transmittance) than ethylene glycol for incident electromagnetic waves 34 having a wavelength 36 in the range from 800 nm to 2200 nm, and in particular in the range between 1400 nm and 1600 nm, and especially at 1550 nm.

EXAMPLES

Several example liquid lens formulations that utilize a conducting liquid 16 that includes an ionic compound with a dicyanamide anion or a tricyanomethanide anion were prepared. The examples reveal a conducting liquid 16 that includes an ionic compound with a dicyanamide anion or a tricyanomethanide anion can have a density that matches (within 0.10 g/cm$^3$ at a temperature, such as at 20 degrees Celsius) the density of the insulating liquid 18. For example, the densities match to within 0.01 g/cm$^3$, within 0.005 g/cm$^3$, or within 0.001 g/cm$^3$. The example formulations were then incorporated into a liquid lens 200, and the transmissivity of the liquid lens 200 (including both the conducting liquid 16 and the insulating liquid 18) was determined as a function of the wavelength 36 of the incident electromagnetic waves 34. The transmissivity of the example liquid lens 200 formulation are compared to the transmissivity of a commercial liquid lens 200 in FIG. 5.

Example 1

In the formulation of Example 1, the conducting liquid 16 is 100 percent by weight 1-ethyl-3-methylimidazolium dicyanamide. The insulating liquid 18 includes dodecane, (25-35% nonafluorohexylmethylsiloxane) (65-75% dimethylsiloxane) copolymer, bis(nonafluorohexyl)tetramethyldisiloxane, and polydimethylsiloxane. Note that the densities of the conducting liquid 16 and the insulating liquid 18 match.

| Conducting liquid 16 | | Insulating liquid 18 | |
|---|---|---|---|
| % by weight | compound | % by weight | compound |
| 100% | 1-ethyl-3-methylimidazolium dicyanamide | 12% | dodecane |
| | | 63% | (25-35% nonafluorohexylmethylsiloxane) (65-75% dimethylsiloxane) copolymer |
| | | 15% | bis(nonafluorohexyl)-tetramethyldisiloxane |
| | | 10% | polydimethylsiloxane |
| Density (20° C.): 1.104 g/cm$^3$ | | Density (20° C.): 1.104 g/cm$^3$ | |
| Viscosity (20° C.): 14.9 cSt | | Viscosity (20° C.): 4.6 cSt | |
| Index (589 nm, 20° C.): 1.516 | | Index (589 nm, 20° C.): 1.375 | |

Example 2

In the formulation of Example 2, the conducting liquid 16 is 100 percent by weight 1-butyl-1-methylpyrrolidinium tricyanomethanide. The insulating liquid 18 includes dodecane, (25-35% nonafluorohexylmethylsiloxane) (65-75% dimethylsiloxane) copolymer, bis(nonafluorohexyl)tetramethyldisiloxane, and polydimethylsiloxane. Note that the densities of the conducting liquid 16 and the insulating 18 match to within 0.001 g/cm$^3$.

| Conducting liquid 16 | | Insulating liquid 18 | |
|---|---|---|---|
| % by weight | compound | % by weight | compound |
| 100% | 1-butyl-1-methylpyrrolidinium tricyanomethanide | 30% | dodecane |
| | | 20% | (25-35% nonafluorohexylmethylsiloxane) (65-75% dimethylsiloxane) copolymer |
| | | 20% | bis(nonafluorohexyl)-tetramethyldisiloxane |
| | | 30% | polydimethylsiloxane |
| Density (20° C.): 1.010 g/cm$^3$ | | Density (20° C.): 1.011 g/cm$^3$ | |
| Viscosity (20° C.): 34.4 cSt | | Viscosity (20° C.): 3.7 cSt | |
| Index (589 nm, 20° C.): 1.499 | | Index (589 nm, 20° C.): 1.387 | |

Example 3

In the formulation of Example 3, the conducting liquid 16 includes 1-ethyl-3-methylimidazolium tricyanomethanide and γ-butyrolactone. The insulating liquid 18 includes dodecane, (25-35% nonafluorohexylmethylsiloxane) (65-75% dimethylsiloxane) copolymer, bis(nonafluorohexyl)tetramethyldisiloxane, and polydimethylsiloxane. Note that the densities of the conducting liquid 16 and the insulating 18 match to within 0.005 g/cm$^3$.

| Conducting liquid 16 | | Insulating liquid 18 | |
|---|---|---|---|
| % by weight | compound | % by weight | compound |
| 80% | 1-ethyl-3-methylimidazolium tricyanomethanide | 15% | dodecane |
| 20% | γ-butyrolactone | 15% | (25-35% nonafluorohexylmethylsiloxane) (65-75% dimethylsiloxane) copolymer |
| | | 60% | bis(nonafluorohexyl)-tetramethyldisiloxane |
| | | 10% | polydimethylsiloxane |
| Density (20° C.): 1.095 g/cm$^3$ | | Density (20° C.): 1.090 g/cm$^3$ | |
| Viscosity (20° C.): 9.2 cSt | | Viscosity (20° C.): 4.2 cSt | |
| Index (589 nm, 20° C.): 1.500 | | Index (589 nm, 20° C.): 1.378 | |

Figure 5:
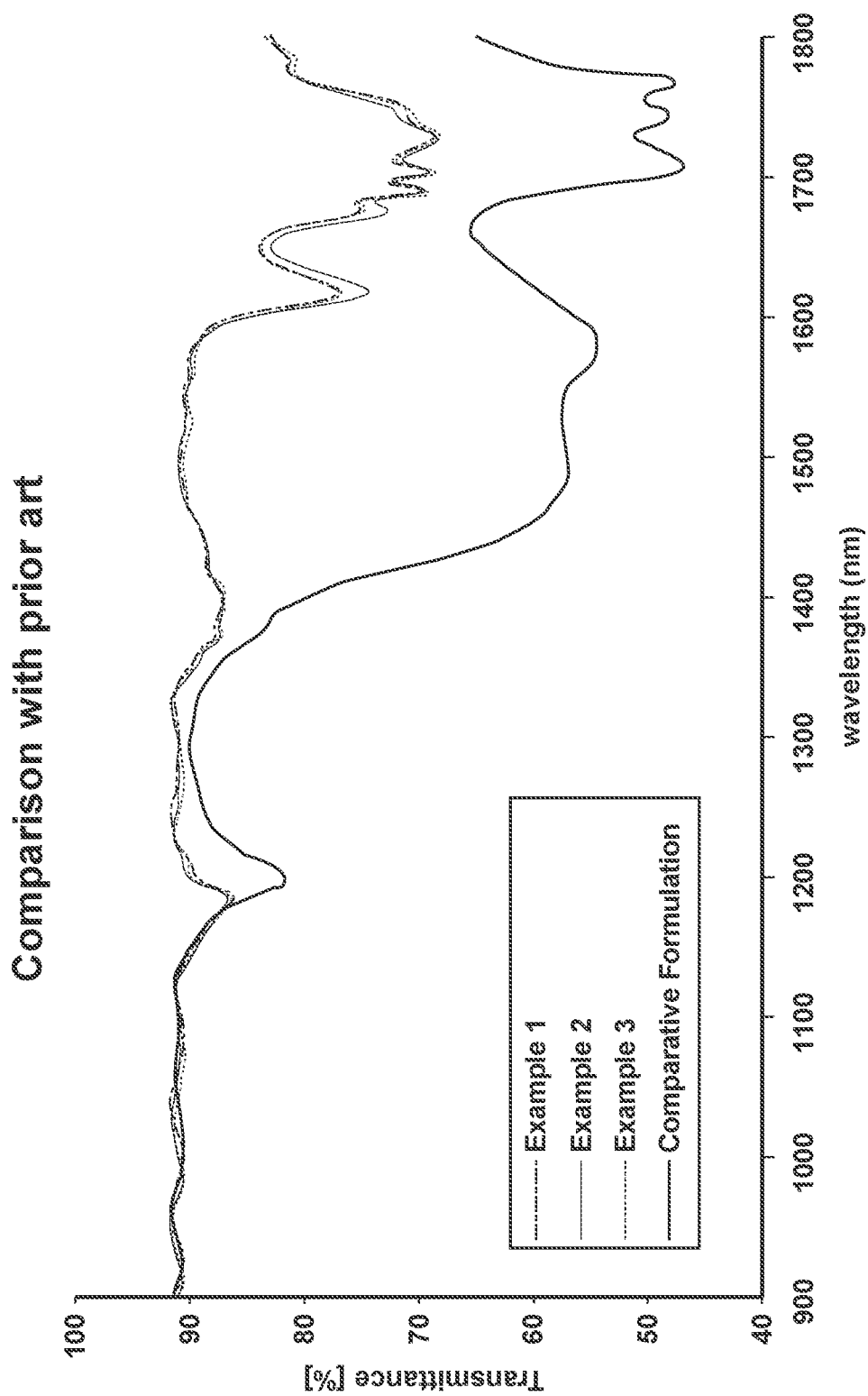
FIG. 5 is a graph of the percentage transmittance of incident electromagnetic waves through several liquid lenses, each utilizing a different conducting liquid and insulating liquid, illustrating improved transmittance of electromagnetic waves having a wavelength in the infrared portion when the conducting liquid includes an ionic compound having either a tricyanomethanide anion or a dicyanamide anion.

Referring now to FIG. 5, the formulation example 1 above was tested to determine transmissivity of the electromagnetic waves 34 through the liquid lens 200, which includes the formulated conducting liquid 16 and the insulating liquid 18, as a function of the wavelength 36 of the incident electromagnetic waves 34. The liquid lenses 200 tested for transmissivity did not include an anti-reflective coating. Utilization of an anti-reflective coating would only increase the transmissivity. The transmissivity of the formulation example 1 is then compared to the transmissivity of a comparative formulation. The comparative formulation is a commercially available liquid lens from Corning® available under the tradename Corning® Varioptic® Lenses and is model A-25H. The Corning® Varioptic® model A-25H variable focus lens utilizes a conducting liquid that includes both water and ethylene glycol.

As the graph of FIG. 5 reveals, formulation example 1 is as transparent to electromagnetic waves 34 having a wavelength 36 in the range of 900 nm to 1150 nm as the comparative formulation. Formulation example 1 is more transparent to electromagnetic waves 34 having a wavelength 36 larger than 1150 nm (including at least the range of 1150 nm to 1800 nm) than the comparative formulation. Formulation example 1 has a transmittance of over 85 percent for electromagnetic waves 34 having a wavelength 36 between 900 nm and about 1570 nm. Formulation example 1 is much more transparent to electromagnetic waves 34 having a wavelength 36 between 1400 nm and 1600 nm than the comparative formulation. For example, the example formulations 1-3 transmit approximately 90% of incident electromagnetic waves 34 having a wavelength 36 of 1550 nm, while the comparative formulation transmits 57% of incident electromagnetic waves 34 at that wavelength 36. The transmittance of 90% of incident electromagnetic waves 34 having a wavelength 36 of 1550 nm is close to the theoretical limit of 92% in the absence of an antireflective coating. In addition, the samples utilized for the transmittance experiments have a thickness that is thicker than some applications for the conductive liquid. Therefore, the level of transmittance for those applications will be higher compared to the results indicated here. Very similar features are expected with formulation examples 2 and 3.

Example 4

In the formulation of Example 4, the conducting liquid 16 includes 1-ethyl-3-methylimidazolium dicyanamide. The insulating liquid 18 includes 1-naphtyltriethylgermane, n-octyltris(trimethylsiloxy)silane, and polyphenylether SANTOLIGHT SL-5267*. Note that the densities match to within 0.008 g/cm$^3$.

| Conducting liquid 16 | | Insulating liquid 18 | |
|---|---|---|---|
| % by weight | compound | % by weight | compound |
| 100% | 1-ethyl-3-methylimidazolium dicyanamide | 85% | 1-naphtyltriethylgermane |
| | | 10% | n-octyltris(trimethylsiloxy)silane |
| | | 5% | polyphenylether SANTOLIGHT SL-5267 ® |
| Density (20° C.): 1.104 g/cm$^3$ | | Density (20° C.): 1.112 g/cm$^3$ (simulated) | |
| Viscosity (20° C.): 14.9 cSt | | Viscosity (20° C.): 10.1 cSt | |
| Index (589 nm, 20° C.): 1.516 | | Index (589 nm, 20° C.): 1.569 | |

Example 5

In the formulation of Example 5, the conducting liquid 16 includes 1-ethyl-3-methylimidazolium dicyanamide. The insulating liquid 18 includes dodecane, (25-35% nonafluorohexylmethylsiloxane) (65-75% dimethylsiloxane) copolymer, bis(nonafluorohexyl)tetramethyldisiloxane, hexamethyldigermane, and hexaethyldigermane.

| Conducting liquid 16 | | Insulating liquid 18 | |
|---|---|---|---|
| % by weight | compound | % by weight | compound |
| 100% | 1-ethyl-3-methylimidazolium dicyanamide | 12% | dodecane |
| | | 33% | (25-35% nonafluorohexylmethylsiloxane) (65-75% dimethylsiloxane) copolymer |
| | | 5% | bis(nonafluorohexyl)-tetramethyldisiloxane |
| | | 20% | hexamethyldigermane |
| | | 30% | hexaethyldigermane |
| Density (20° C.): 1.104 g/cm$^3$ | | Density (20° C.): 1.136 g/cm$^3$ (simulated) | |
| Viscosity (20° C.): 14.9 cSt | | Viscosity (20° C.): 3.6 cSt | |
| Index (589 nm, 20° C.): 1.516 | | Index (589 nm, 20° C.): 1.430 | |

Example 6

In the formulation of Example 6, the conducting liquid 16 includes 1-ethyl-3-methylimidazolium dicyanamide. The insulating liquid 18 includes n-octyltris(trimethylsiloxy)silane, hexamethyldigermane, and hexaethyldigermane.

| Conducting liquid 16 | | Insulating liquid 18 | |
|---|---|---|---|
| % by weight | compound | % by weight | compound |
| 100% | 1-ethyl-3-methylimidazolium dicyanamide | 14% | n-octyltris(trimethylsiloxy)silane |
| | | 50% | hexaethyldigermane |
| | | 36% | hexamethyldigermane |
| Density (20° C.): 1.104 g/cm$^3$ | | Density (20° C.): 1.106 g/cm$^3$ (simulated) | |
| Viscosity (20° C.): 14.9 cSt | | Viscosity (20° C.): 1.9 cSt | |
| Index (589 nm, 20° C.): 1.516 | | Index (589 nm, 20° C.): 1.472 | |

Figure 6:
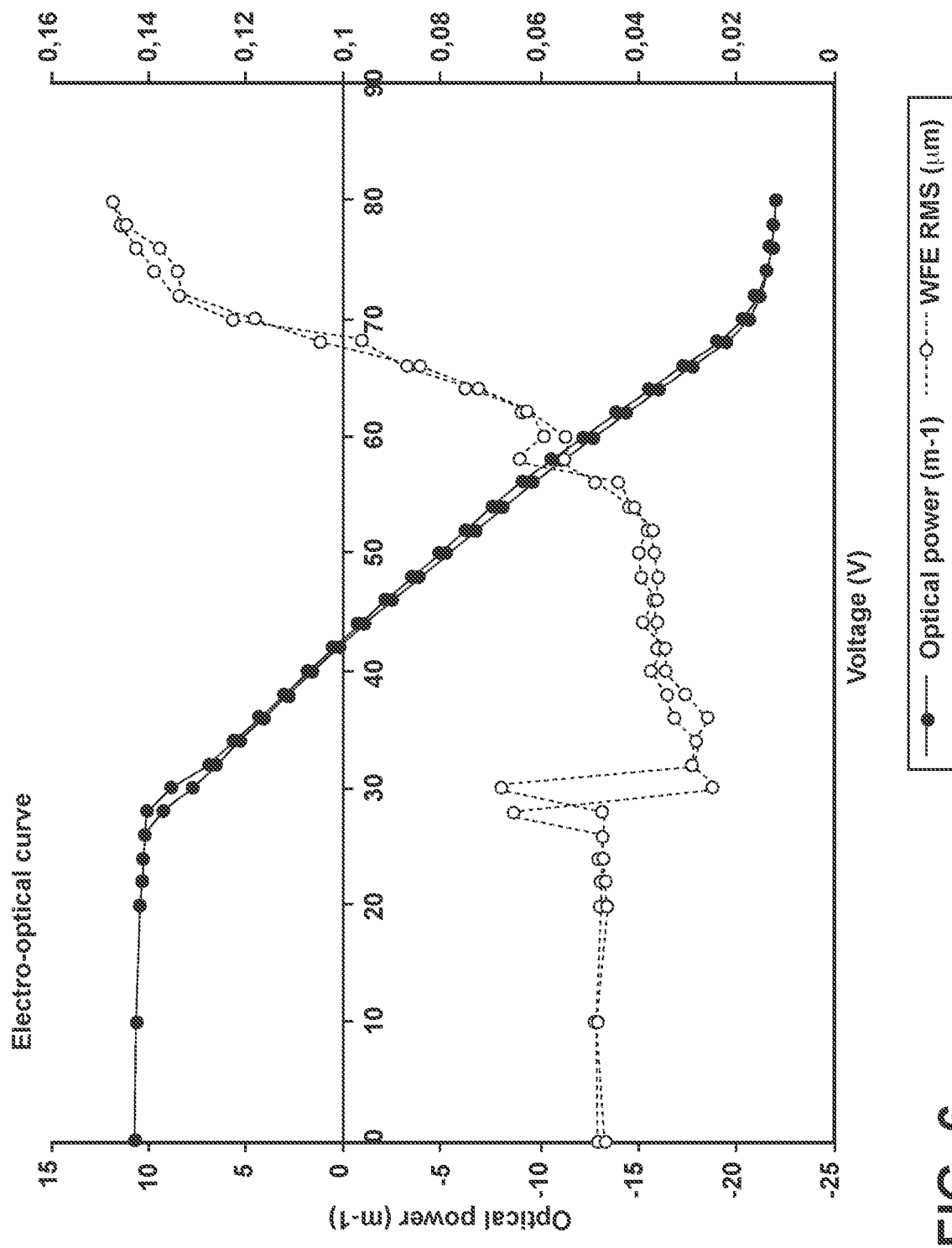
FIG. 6 is a graph of optical power as a function of voltage (electrowetting curve), and wavefront error as a function of voltage, for a liquid lens incorporating a conducting liquid of the present disclosure.

The conducting liquid 16 and the insulating liquid 18 of Example 6 were incorporated into a liquid lens 200. An electrowetting curve illustrating optical power and wavefront error as a function of voltage applied to the liquid lens 10 is illustrated at FIG. 6. In the −5D to +15D diopter range, the hysteresis of the lenses are calculated at 0.6D maximum. The optical quality as quantified by the root-mean-squared wavefront error (RMS WFE) is 65 nm maximum. Those values were measured on a 2.5 m clear aperture.

A person skilled in the art would note that in examples 1, 2, 3, 5, and 6 the conducting liquid 16 has a higher optical index than the insulating liquid 18. The corresponding liquid lens 10 would be convergent at low voltage and become divergent at higher voltages. In example 4, the conducting liquid 16 has a lower optical index than the insulating liquid 18. The corresponding liquid lens 10 would be divergent at low voltage and become convergent at higher voltages. Any type of situation could be used to design optical systems with an autofocus, or tilt, or higher aberration correction using the liquid lens, provided the sign of the variation of the driven parameter with voltage is considered in the design of the full system.

In examples 1, 2, 4, 5, and 6, above, the ionic compound is 100% by weight of the conducting liquid 16. In example 3, the ionic compound is 80% by weight of the conducting liquid 16. In some embodiments, the ionic compound is at least 80% by weight of the conducting liquid 16, at least 85% by weight of the conducting liquid 16, at least 90% by weight of the conducting liquid 16, at least 95% by weight of the conducting liquid 16, at least 97% by weight of the conducting liquid 16, or approximately 100% or 100% by weight of the conducting liquid 16. Manufacturing processes utilized to make the ionic compound may result in trace amounts of impurities such as water being present in the liquid presented as the ionic compound.

It will be apparent to those skilled in the art that various modifications and variations can be made without departing from the spirit or scope of the claims.

What is claimed is:

1. A liquid lens comprising:
a lens body comprising a cavity; and
a conducting liquid and an insulating liquid disposed within the cavity, the conducting liquid being substantially immiscible with the insulating liquid, whereby an interface is defined between the conducting liquid and the insulating liquid;
wherein the conducting liquid comprises an ionic compound of either a dicyanamide anion and a cation counterion, or a tricyanomethanide anion and a cation counterion, the dicyanamide anion having the general formula

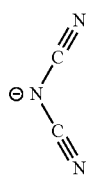

the tricyanomethanide anion having the general formula

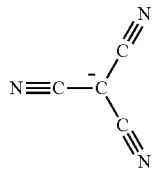

and the cation counterion is one of an imidazolium, a pyrrolidininium, a piperidinium, a phosphonium, a pyridinium, a pyrrolinium, or a sulfonium cation;
wherein a density of the conducting liquid is within 0.10 g/cm$^3$ of a density of the insulating liquid at 20 degrees Celsius;
wherein at least one of the density of the conducting liquid or the density of the insulating liquid is about or greater than 1.0 g/cm$^3$ at 20 degrees Celsius.

2. The liquid lens of claim 1, wherein, the conducting liquid is in a liquid phase between −20 degrees Celsius and 70 degrees Celsius.

3. The liquid lens of claim 1, wherein, the cation counterion is one of 1-ethyl-3-methylimidazolium cation, 1-allyl-3-methylimidazolium cation, 1-benzyl-3-methylimidazolium cation, 1-butyl-3-methylimidazolium cation, 1-hexyl-3-methylimidazolium cation, 1-ethyl-3-methylimidazolium cation, N-ethyl-N-methylpyrrolidinium cation, 1-butyl-1-methylpyrrolidinium cation, or trihexyltetradecylphosphonium cation.

4. The liquid lens of claim 1, wherein, the ionic compound of the conducting liquid is one of N-ethyl-N-methylpyrrolidinium dicyanamide, 1-ethyl-3-methylimidazolium dicyanamide, 1-butyl-1-methylpyrrolidinium tricyanomethanide, or 1-ethyl-3-methylimidazolium tricyanomethanide.

5. The liquid lens of claim 1, wherein the conducting liquid has a transmittance of at least 50% over a thickness of 1 mm for electromagnetic waves having a wavelength of 1550 nm.

6. The liquid lens of claim 1, wherein the conducting liquid has a transmittance of at least 90% for electromagnetic waves having a wavelength of 1550 nm.

7. The liquid lens of claim 1, wherein the ionic compound is at least 97 percent by weight of the total weight of the conducting liquid.

8. The liquid lens of claim 1, wherein:
the insulating liquid comprises dodecane, (25-35% nonafluorohexylmethylsiloxane) (65-75% dimethylsiloxane) copolymer, bis(nonafluorohexyl) tetramethyldisiloxane, and polydimethylsiloxane; and
the ionic compound of the conducting liquid is 1-butyl-1-methylpyrrolidinium tricyanomethanide.

9. The liquid lens of claim 1, wherein:
the insulating liquid comprises dodecane, (25-35% nonafluorohexylmethylsiloxane) (65-75% dimethylsiloxane) copolymer, bis(nonafluorohexyl) tetramethyldisiloxane, hexamethyldigermane, and hexaethyldigermane; and
the ionic compound of the conducting liquid is 1-ethyl-3-methylimidazolium dicyanamide.

10. The liquid lens of claim 1, wherein the insulating liquid comprises greater than or equal to 12% and less than or equal to 30% hydrocarbon.

11. The liquid lens of claim 10, wherein the hydrocarbon comprises dodecane.

12. The liquid lens of claim 1,
wherein the insulating liquid comprises at least one of a fluorinated Si-based compound or a Ge-based compound.

13. The liquid lens of claim 12, wherein the insulating liquid comprises the fluorinated Si-based compound, and wherein a refractive index of the insulating liquid is less than or equal to 1.430.

14. The liquid lens of claim 13, wherein the insulating liquid comprises at least 38% of the fluorinated Si-based compound.

15. The liquid lens of claim 13, wherein the fluorinated Si-based compound has formula (Ia), (Ib), and/or (Ic)

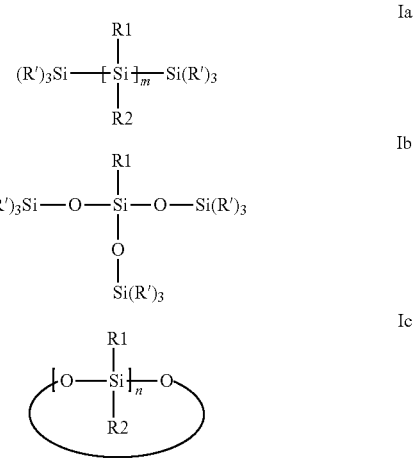

wherein:
each of R1, R2 and R' independently represents alkyl, (hetero)aryl, (hetero)arylalkyl, (hetero)arylalkenyl, or (hetero)arylalkynyl;
m is between 1 and 20; and
in formula (Ic), n is greater than 2.

16. The liquid lens of claim 12, wherein the insulating liquid comprises the Ge-based compound, and wherein a refractive index of the conducting liquid is greater than a refractive index of the insulating liquid.

17. The liquid lens of claim 1,
wherein the insulating liquid comprises a Si-based compound; and
wherein a refractive index of the insulating liquid is less than or equal to 1.472.

18. The liquid lens of claim 17, wherein the refractive index of the insulating liquid is less than or equal to 1.43.

19. The liquid lens of claim 17, wherein the Si-based compound comprises at least one of hexamethyidisilane, diphenyldimethylsilane, chlorophenyltrimethylsilane, phenyltrimethyl-silane, phenethyltris(trimethylsiloxy) silane, phenyltris(trimethylsiloxy) silane, polydimethylsiloxane, tetraphenyltetramethyltrisiloxane, poly (3,3,3-trifluoropropylmethylsiloxane), 3,5,7-triphenylnonamethyl-pentasiloxane, 3,5-diphenyloctamethyltetrasiloxane, 1,1,5,5-tetraphenyl-1,3,3,5-tetramethyl-trisiloxane, hexamethylcyclotrisiloxane, n-octyltris(trimethylsiloxy)silane, or bis(nonafluorohexyl)tetramethyldisiloxane and (25-35% nonafluorohexylmethylsiloxane) (65-75% dimethylsiloxane) copolymer.

* * * * *